US012789822B2

United States Patent
Ogawa et al.

(10) Patent No.: US 12,789,822 B2
(45) Date of Patent: Nov. 10, 2026

(54) VEHICLE OCCUPANT MENTAL STATE INDUCING APPARATUS

(71) Applicant: Panasonic Intellectual Property Management Co., Ltd., Osaka (JP)

(72) Inventors: Kenji Ogawa, Osaka (JP); Takeichi Shinya, Osaka (JP); Tadahiro Kugimaru, Osaka (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 0 days.

(21) Appl. No.: 18/807,337

(22) Filed: Aug. 16, 2024

(65) Prior Publication Data

US 2024/0400069 A1 Dec. 5, 2024

Related U.S. Application Data

(63) Continuation of application No. PCT/JP2022/041424, filed on Nov. 7, 2022.

(30) Foreign Application Priority Data

Feb. 22, 2022 (JP) ................................ 2022-025945

(51) Int. Cl.
*B60W 50/00* (2006.01)
*A61M 21/00* (2006.01)
(Continued)

(52) U.S. Cl.
CPC ........ *B60W 50/0098* (2013.01); *A61M 21/02* (2013.01); *B60J 1/2011* (2013.01);
(Continued)

(58) Field of Classification Search
None
See application file for complete search history.

(56) References Cited

U.S. PATENT DOCUMENTS 10,004,873 B1 * 6/2018 Hur ...................... A61B 5/6893
11,685,303 B2 * 6/2023 Currier ..................... B60P 3/38
296/190.02

(Continued)

FOREIGN PATENT DOCUMENTS

DE 102015122245 A1 6/2017
JP 2010068941 A * 4/2010

(Continued)

OTHER PUBLICATIONS

International Search Report, dated Jan. 24, 2023, for International Patent Application No. PCT/JP2022/041424. (4 pages) (with English translation).

(Continued)

*Primary Examiner* — Peter D Nolan
*Assistant Examiner* — Jacob Kent Besteman-Street
(74) *Attorney, Agent, or Firm* — Seed Intellectual Property Law Group LLP

(57) ABSTRACT

An inducing apparatus includes: an inducer that induces an inducing subject in a vehicle to a predetermined mental state, the inducer being provided within a field of view of the inducing subject, being capable of blocking outside-vehicle information within the field of view, and being capable of operating to induce the mental state; and a processor that controls the inducer to transition the mental state of the inducing subject.

12 Claims, 6 Drawing Sheets

(51) Int. Cl.

| | |
|---|---|
| ***A61M 21/02*** | (2006.01) |
| ***B60J 1/20*** | (2006.01) |
| ***B60J 3/04*** | (2006.01) |
| ***B60W 40/08*** | (2012.01) |

(52) U.S. Cl.

CPC ................ *B60J 3/04* (2013.01); *B60W 40/08* (2013.01); *A61M 2021/0016* (2013.01); *A61M 2021/0027* (2013.01); *A61M 2021/0044* (2013.01); *B60W 2540/22* (2013.01); *B60W 2540/221* (2020.02)

(56) References Cited

U.S. PATENT DOCUMENTS

| | | | | |
|---|---|---|---|---|
| 2012/0253221 | A1* | 10/2012 | Hamaguchi .............. | A61B 5/00<br>600/544 |
| 2015/0251661 | A1* | 9/2015 | Mathissen ....... | B60W 30/18054<br>701/45 |
| 2016/0176409 | A1* | 6/2016 | Kirsch ................... | B60N 2/919<br>701/1 |
| 2017/0189640 | A1* | 7/2017 | Sadwick ............... | A61M 21/02 |
| 2018/0284932 | A1* | 10/2018 | Nehmad ................ | B60K 35/10 |
| 2020/0121889 | A1* | 4/2020 | Noda .................... | A61M 21/00 |
| 2020/0359954 | A1* | 11/2020 | Sunagawa ............. | A61B 5/162 |
| 2020/0377041 | A1 | 12/2020 | Sekizuka | |
| 2021/0398562 | A1* | 12/2021 | Verbeke ................. | B60K 35/28 |
| 2022/0203809 | A1 | 6/2022 | Shimonomoto et al. | |
| 2022/0324458 | A1* | 10/2022 | Neubecker ............. | G06N 20/00 |
| 2023/0001129 | A1* | 1/2023 | Ito .......................... | A47C 7/748 |
| 2023/0001139 | A1* | 1/2023 | Otake ............... | A61M 25/0041 |
| 2023/0173953 | A1 | 6/2023 | Miyoshi et al. | |

FOREIGN PATENT DOCUMENTS

| | | | | | |
|---|---|---|---|---|---|
| JP | 2010099410 | A | * | 5/2010 | |
| JP | 5152570 | B2 | * | 2/2013 | |
| JP | 2015019857 | A | * | 2/2015 | |
| JP | 2017109635 | A | | 6/2017 | |
| JP | 2018177188 | A | | 11/2018 | |
| JP | 2020192887 | A | | 12/2020 | |
| JP | 2021020671 | A | | 2/2021 | |
| JP | 2022185633 | A | | 12/2022 | |
| WO | 2007011060 | A1 | | 1/2007 | |
| WO | 2017102614 | A1 | | 6/2017 | |
| WO | 2018057980 | A1 | | 3/2018 | |
| WO | WO-2018225472 | A1 | * | 12/2018 | ............... B60N 3/00 |
| WO | WO 2021187495 | A1 | | 9/2021 | |

OTHER PUBLICATIONS

Extended European Search Report, dated May 19, 2025, for European Patent Application No. 22928877.4. (12 pages).

* cited by examiner

VEHICLE OCCUPANT MENTAL STATE INDUCING APPARATUS

TECHNICAL FIELD

The present disclosure relates to an inducing apparatus.

BACKGROUND ART

An apparatus has been known that induces a mental state of an occupant (inducing subject) who gets in a vehicle by adjusting an in-vehicle environment. For example, Japanese Patent No. 5152570 discloses a system in which a state transition pattern having a base mental state matching a current mental state of a user is selected, and contents of inducing hospitality operations are read out and sequentially performed in accordance with the state transition pattern.

CITATION LIST

Patent Literature

PTL 1

Japanese Patent No. 5152570

SUMMARY OF INVENTION

Technical Problem

However, in the configuration described in Japanese Patent No. 5152570, for example, the inducing subject can see outside-vehicle information from the window of the vehicle, which possibly interferes with the induction of the mental state due to the outside-vehicle information, and thus there is room for improvement as a configuration for inducing the mental state.

An object of the present disclosure is to provide an inducing apparatus capable of appropriately inducing a mental state of an inducing subject.

Solution to Problem

An inducing apparatus according to the present disclosure includes:

- an inducer that induces an inducing subject in a vehicle to a predetermined mental state, the inducer being provided within a field of view of the inducing subject, being capable of blocking outside-vehicle information within the field of view, and being capable of operating to induce the mental state; and
- a processor that controls the inducer to transition the mental state of the inducing subject.

According to the present disclosure, it is possible to appropriately induce a mental state of an inducing subject.

DESCRIPTION OF EMBODIMENTS

Embodiment

Figure 1:
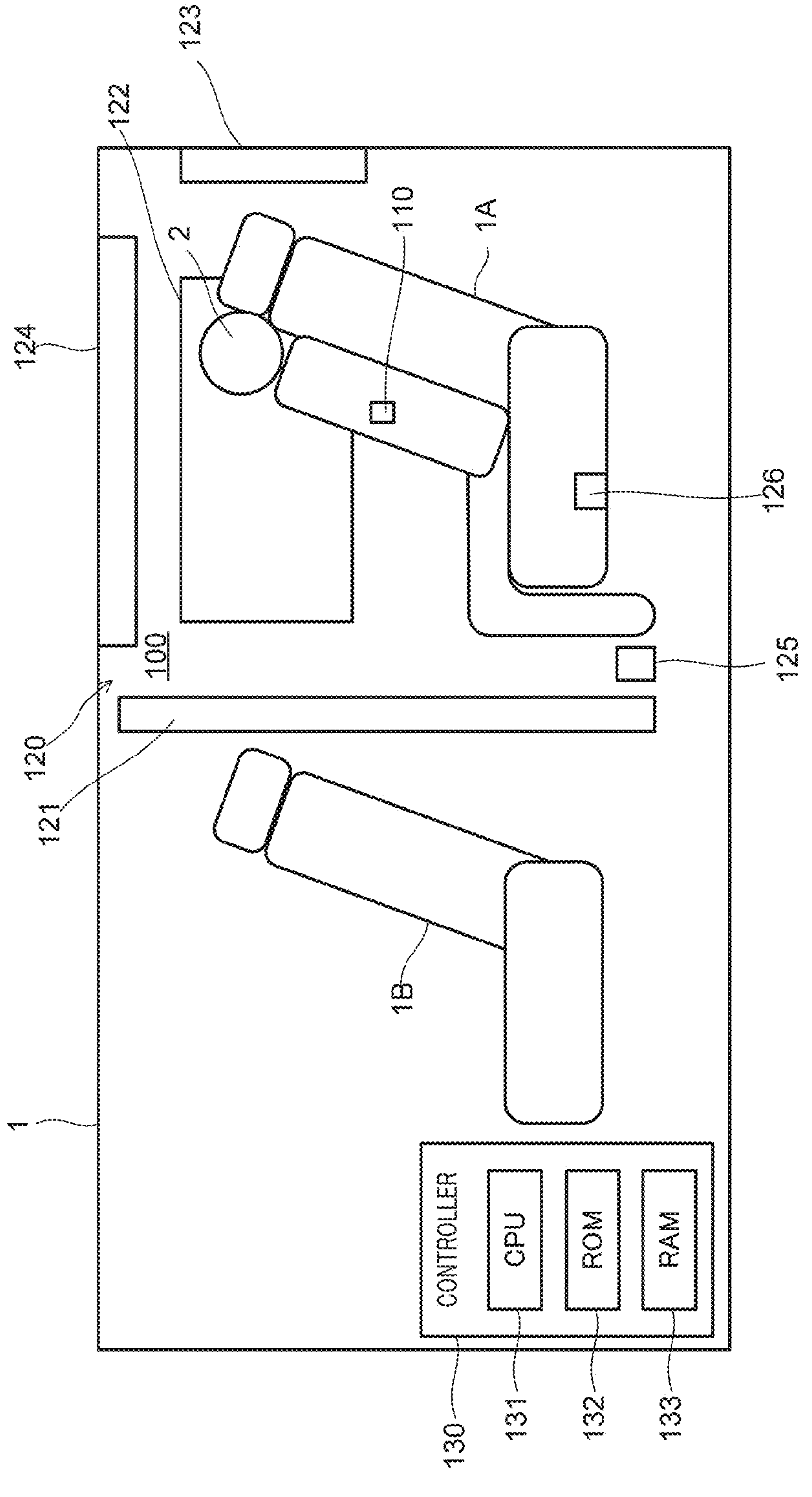
FIG. 1 illustrates an exemplary configuration of an inducing apparatus according to an embodiment of the present disclosure.

Hereinafter, an embodiment of the present disclosure will be described in detail based on the drawings. FIG. 1 illustrates an exemplary configuration of inducing apparatus 100 according to an embodiment of the present disclosure.

As illustrated in FIG. 1, inducing apparatus 100 is an apparatus that is mounted in vehicle 1 and induces a mental state of inducing subject 2 seated on back seat 1A to a predetermined state. The predetermined state is, for example, a relaxed state or an awaking state.

Figure 2:
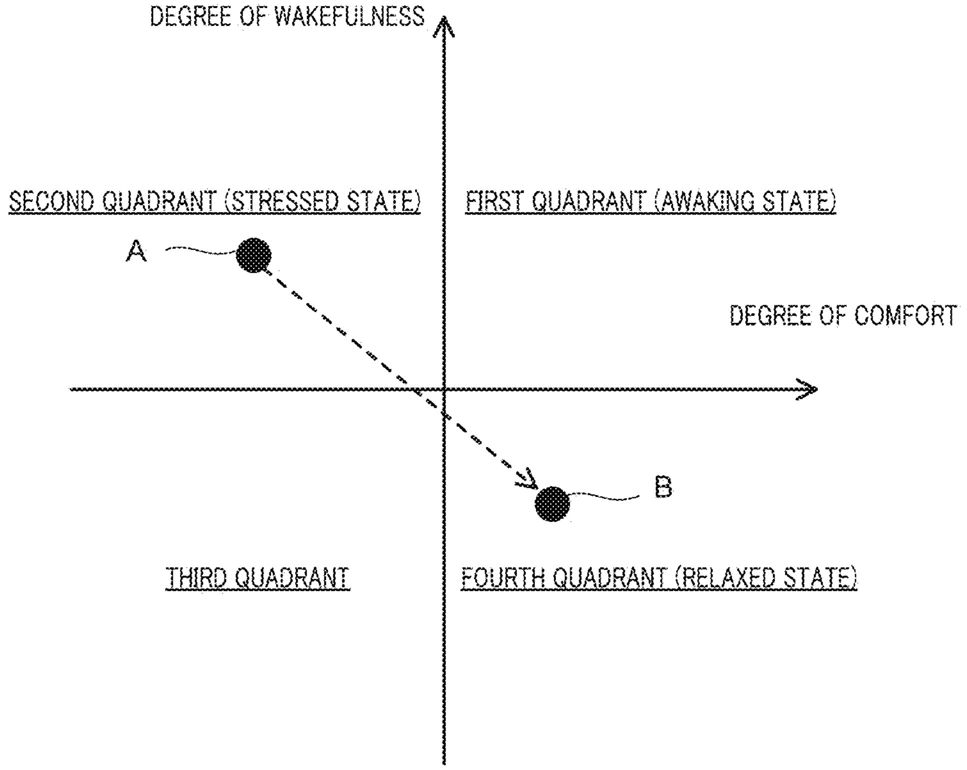
FIG. 2 illustrates an exemplary transition of a mental state in a mental coordinate system.

A human mental state can be expressed by, for example, a two-dimensional coordinate system (hereinafter, referred to as a mental coordinate system) in which the degree of comfort is indicated by a horizontal axis and the degree of wakefulness is indicated by a vertical axis, as illustrated in FIG. 2. The mental coordinate system indicates a comfortable mood toward the positive side of the horizontal axis (right side in FIG. 2), and indicates an uncomfortable mood toward the negative side of the horizontal axis (left side in FIG. 2). Further, the mental coordinate system indicates a state of awaking without sleepiness toward the positive side (upper side in FIG. 2) of the vertical axis, and indicates a state in which the degree of sleepiness increases toward the negative side (lower side in FIG. 2) of the vertical axis. Furthermore, the first quadrant of the mental coordinate system is a region in which the horizontal coordinate and the vertical coordinate are positive, and the second quadrant is a region in which the horizontal coordinate is negative and the vertical coordinate is positive. In addition, the third quadrant of the mental coordinate system is a region in which the horizontal coordinate and the vertical coordinate are negative, and the fourth quadrant is a region in which the horizontal coordinate is positive and the vertical coordinate is negative.

The relaxed state is a state in which inducing subject 2 is relaxed while the degrees of tension and fatigue are relieved, and corresponds to the fourth quadrant in the mental coordinate system corresponding to a state in which inducing subject 2 feels conformable and the degree of sleepiness is high.

The awaking state is a state in which inducing subject 2 is in a good mental and physical condition and can perform well when performing a predetermined action, and corresponds to the first quadrant in the mental coordinate system corresponding to a state of being in a comfortable mood and awake.

For example, inducing subject 2 possibly gets in vehicle 1 in a stressed state, in which inducing subject 2 is stressed out. The stressed state is a state in which the degrees of tension and fatigue are relatively high, and corresponds to the second quadrant in the mental coordinate system corresponding to a state of being awake and in an uncomfortable mood. Point A illustrated in FIG. 2 indicates a mental state of inducing subject 2 when he/she gets in vehicle 1, and is located in the region of the second quadrant (stressed state).

Inducing apparatus 100, for example, relieves the stress of inducing subject 2 in the stressed state and induces inducing subject 2 to a relaxed state. That is, inducing apparatus 100 transitions the mental state (point A) of the inducing subject to any position (e.g., point B) in the region of the fourth quadrant (relaxed state).

Figure 3A:
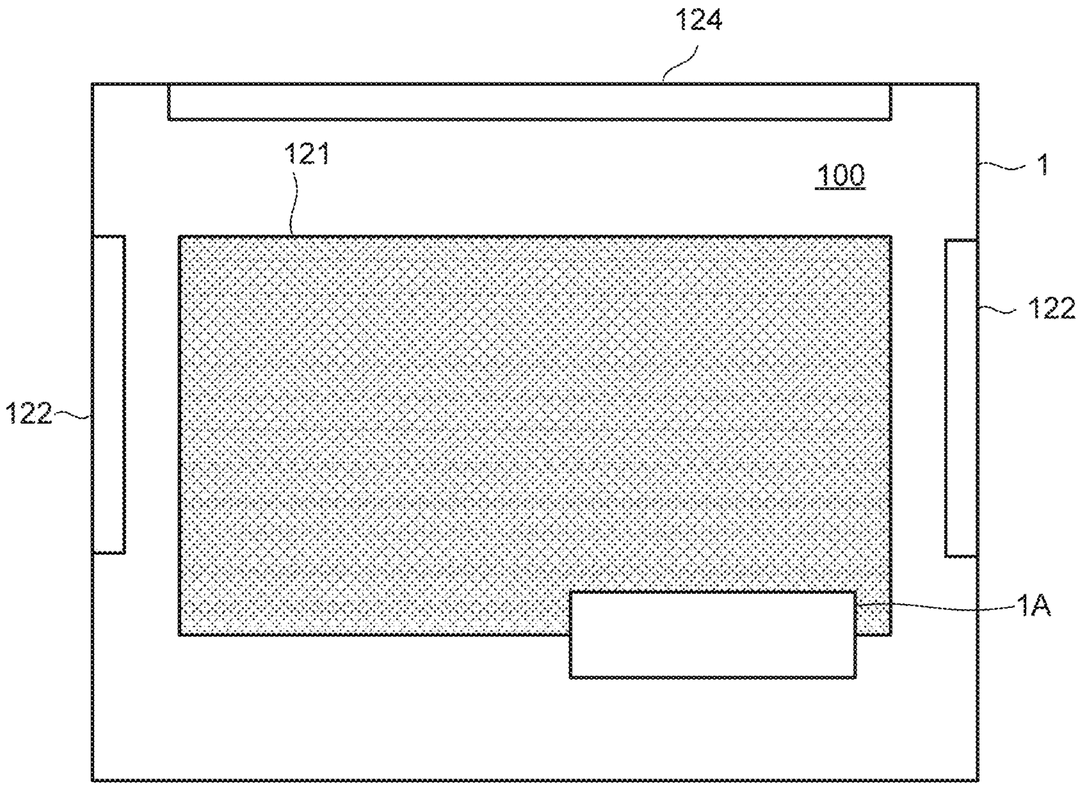
FIG. 3A illustrates a partition in a blocking state seen from a rear side.
Figure 3B:
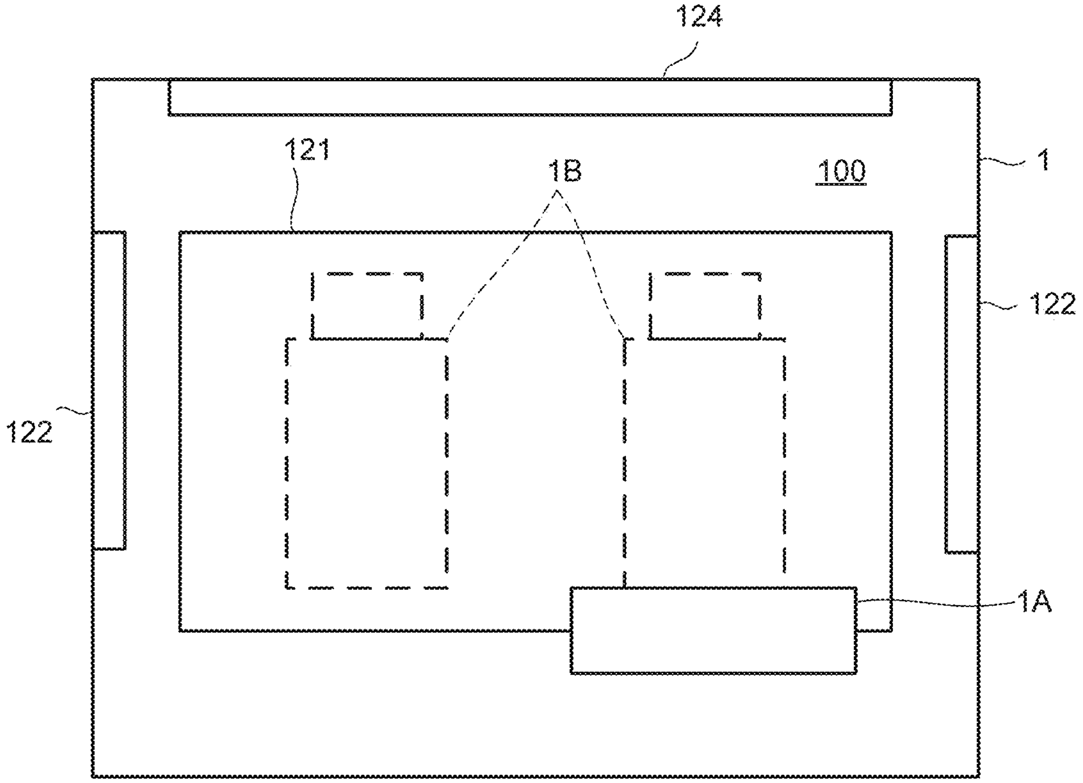
FIG. 3B illustrates the partition in a non-blocking state seen from the rear side.

Further, inducing apparatus 100 induces inducing subject 2 to the awaking state so that inducing subject 2 can perform well at the destination. As illustrated in FIGS. 1, 3A, and 3B, inducing apparatus 100 includes information acquirer 110, inducer 120, and controller 130. FIGS. 3A and 3B each illustrate an anterior area viewed from the side of inducing subject 2 seated on back seat 1A.

Information acquirer 110 acquires a measurement result of state information to be an indicator for determining a change in the mental state of inducing subject 2. For example, the state information may be information capable of estimating a change in the mental state of inducing subject 2, such as heart rate information, pulse information, respiration information, blood pressure information, electrocardiogram information, electroencephalogram information, body surface temperature information, pupil diameter information, electromyogram information, and body movement information.

Information acquirer 110 may be a relatively small measurement device capable of measuring the state information and capable of being mounted in vehicle 1, or may acquire the state information from another measuring device. The measurement device may be of a contact type or a non-contact type. The measurement device may also be a wearable device or the like. For example, known measurement devices may be used for the heart rate information, pulse information, respiration information, blood pressure information, electrocardiogram information, electroencephalogram information, body surface temperature information, electromyogram information, and the like. Further, the body surface temperature information, the pupil diameter information, and the body movement information may be measured based on an image captured by an imaging device.

The position of the mental state of inducing subject 2 in the mental coordinate system can be determined according to the change in the state information.

For example, it is conventionally known that a phenomenon is observed in which sleepiness of a driver changes in response to a change in pulse wave information (pulse information).

It is also conventionally known that the degree of comfort of the person being treated changes in response to a change in the electroencephalogram information.

Furthermore, although it is a subjective evaluation, it has been experimentally confirmed that, when the skin temperature (body surface temperature information) of inducing subject 2 increases, the mental state of inducing subject 2 transitions to a comfortable side, and when the skin temperature of inducing subject 2 decreases, the mental state of inducing subject 2 transitions to the side where the degree of wakefulness increases.

As described above, acquiring the state information makes it possible to detect the change in the mental state of inducing subject 2.

Information acquirer 110 acquires one or more measurement results of heart rate information, pulse information, respiration information, blood pressure information, electrocardiogram information, electroencephalogram information, body surface temperature information, pupil diameter information, electromyogram information, and body movement information. Note that information acquirer 110 according to the present embodiment does not particularly limit the number of pieces of state information to be acquired, but it is preferred to acquire two or more pieces of state information from the viewpoint that it is easy to determine a change in the mental state of inducing subject 2.

Inducer 120 is mounted in vehicle 1 and is for inducing the mental state of inducing subject 2 to a predetermined state. In one embodiment, inducer 120 includes partition 121, a pair of side sections 122, rear section 123, lighting 124, music player 125, and scent generator 126.

Partition 121, the pair of side sections 122, and rear section 123 may each be a transparent display including, for example, a plurality of glass plates and a display module interposed between the plurality of glass plates. The display module may be composed of a light control panel that has translucency and is configured to be switchable between a transparent state in which light is transmitted and a non-transparent state in which light is not transmitted compared to the transparent state.

That is, partition 121, the pair of side sections 122, and rear section 123 may be configured to be switchable between a transparent state (non-blocking state) and a non-transparent state (blocking state), and may be capable of operating while synchronizing with each other.

Partition 121 is located at the boundary between front seat 1B and back seat 1A of vehicle 1, and is located in the forward field of view of inducing subject 2. Specifically, partition 121 is provided over the area ahead of inducing subject 2, and when partition 121 becomes non-transparent, partitions 21 blocks outside-vehicle information of vehicle 1 in front of inducing subject 2 (see FIG. 3A). The outside-vehicle information is information outside vehicle 1 seen through the windows of vehicle 1. In FIG. 3A, partition 121 is in a non-transparent state (blocking state), so that the area of front seat 1B of vehicle 1 and the area ahead of vehicle 1 supposed to be seen from the windshield cannot be seen from inducing subject 2.

In addition, when partition 121 is transparent, partition 121 does not block outside-vehicle information of vehicle 1 in front of inducing subject 2 (see FIG. 3B). In FIG. 3B, partition 121 is in a transparent state (non-blocking state), so that the area of front seat 1B of vehicle 1 and the area ahead of vehicle 1 supposed to be seen from the windshield can be seen from inducing subject 2.

The pair of side sections 122 is provided on windows of vehicle 1 on both the left and right sides of inducing subject 2 and provided in the field of view of inducing subject 2 when he/she faces the sides. When the pair of side sections 2 is non-transparent, the pair of side sections 122 blocks outside-vehicle information of vehicle 1 on both the left and right sides of inducing subject 2. Further, when the pair of side sections 122 is transparent, the pair of side sections 122 does not block outside-vehicle information of vehicle 1 on both the left and right sides of inducing subject 2.

Rear section 123 is placed at a window of vehicle 1 behind inducing subject 2 and provided in the field of view of inducing subject 2 when he/she faces rearward. When rear section 123 is non-transparent, rear section 123 blocks outside-vehicle information of vehicle 1 behind inducing subject 2. Further, when rear section 123 is transparent, rear section 123 does not block outside-vehicle information of vehicle 1 behind inducing subject 2.

Partition 121, the pair of side sections 122, and rear section 123 can output image information through the display module described above. The image information may include information displayed during a relaxation period, information displayed during an awaking period, and information displayed during a stress transition period to be described later.

The information displayed during the relaxation period is, for example, information that causes inducing subject 2 to relax, such as natural scenery (scenery with much greenery, a small stream of a river, a landscape of mountains, or the like).

The information displayed during the awaking period is, for example, information that causes inducing subject 2 to be conscious of waking up and induces inducing subject 2 to the awaking state, such as the morning sun or mountain flowers.

The information displayed during the stress transition period is, for example, information that stimulates inducing subject 2 to make inducing subject 2 in a stressed state, such as an excitatory color image.

Lighting 124 is a lighting device capable of adjusting the brightness of a space where inducing subject 2 is located, and, for example, may be provided on the ceiling of vehicle 1 over the entire space corresponding to back seat 1A. Lighting 124 may be capable of illuminating the space where inducing subject 2 is located not only with the different degrees of brightness of lights but with special lighting, such as a blue sky or sunlight filtering through trees in the forest during the relaxation period and an excitatory color during the stress transition period.

Music player 125 is a device that reproduces music data stored in advance in a space where inducing subject 2 is located, and includes a speaker device and the like provided at appropriate positions in a space corresponding to back seat 1A. The music data may, for example, include the following sounds: natural sounds combined with background music (BGM) in the relaxation period; lively, cheerful, and active music in the awaking period; and unsettled and frustrating sounds such as a metronome sound, road noise, talking voice, and the like in the stress transition period.

Scent generator 126 is a device that generates a scent in a space where inducing subject 2 is located, and is provided in a space corresponding to back seat 1A in vehicle 1. Examples of the scent may include a healing aroma in the relaxation period, a citrus aroma in the awaking period.

Controller 130 includes Central Processing Unit (CPU) 131, Read Only Memory (ROM) 132, Random Access Memory (RAM) 133, and an input/output circuit, and controls inducer 120 to induce the mental state of inducing subject 2 to a predetermined state based on a preset program.

Specifically, controller 130 controls inducer 120 so that the mental state transitions from the initial mental state of inducing subject 2 to the stressed state, the relaxed state, and the awaking state in this order.

Figure 4:
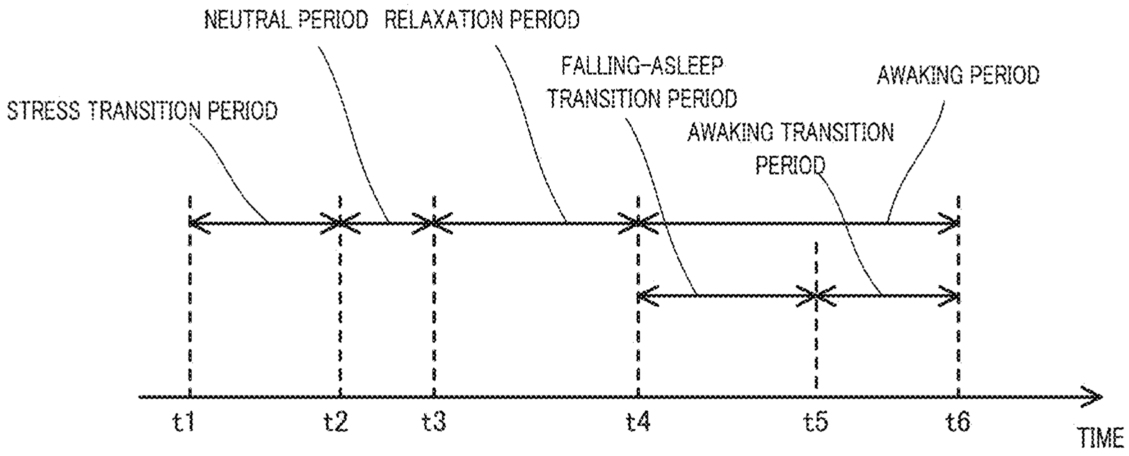
FIG. 4 illustrates time transition in each period.

For example, as illustrated in FIG. 4, it is assumed that inducing subject 2 gets in vehicle 1 (time t1) and desires to relax in vehicle 1. Inducing subject 2 is made in a state in which the state information can be acquired by information acquirer 110, for example, and is seated on back seat 1. An inducing subject 2 who gets in vehicle 1 may recognize that his/her mental state is at least subjectively a stressed state. Note that partition 121 at this time may be in a transparent state or a non-transparent state.

The state information acquired herein may be one or more pieces of the above state information, such as a body surface temperature and a heart rate.

First, controller 130 identifies the mental state of inducing subject 2 based on the change in the acquired state information at the time when the travel of vehicle 1 is started. When the mental state based on the state information at the time when the travel of vehicle 1 is started is a state other than the relaxed state, controller 130 provides a stress transition period in which inducing subject 2 is made in a stressed state.

The stress transition period is a period during which the mental state of inducing subject 2 is transitioned in order to align inducing subject 2 with a predetermined stressed state.

The reason for aligning inducing subject 2 with a predetermined stressed state is to make it easy for inducing subject 2 to realize that inducing subject 2 is relaxed by relatively increasing the transitional amount of the mental state from a predetermined position of the stressed state to a predetermined position of the relaxed state in the mental coordinate system.

The stressed state in the mental coordinate system is the mental state set by inducing apparatus 100. For example, even when inducing subject 2 recognizes that he/she is subjectively in a stressed state, he/she is possibly in an awaking state corresponding to the first quadrant or in a state of the region of the third quadrant in the mental coordinate system. Thus, controller 130 performs control so as to induce inducing subject 2 to a predetermined stressed state in the mental coordinate system first.

In order to induce the inducing subject from a mental state other than the relaxed state to a stressed state, specifically, controller 130 may set partition 121, the pair of side sections 122, and rear section 123 to a non-transparent state (blocking state). Controller 130 may then display, for example, images with excitatory colors on partition 121, the pair of side sections 122, and rear section 123.

In addition to the images, controller 130 may output special lighting with excitatory colors by lighting 124, may generate unsettled and frustrating sounds such as a metronome sound by music player 125, or may output a combination of two or more of the image, lighting, and sound.

Note that the operation contents of inducer 120 in a stress transition period include an action decreasing the degree of comfort and increasing the degree of wakefulness in the mental coordinate system. The operation contents are not limited to the above examples and may be appropriately set according to an experiment or the like.

As described above, the mental state of inducing subject 2 is induced to a stressed state regardless of which area in the mental coordinate system the initial mental state of inducing subject 2 is located in.

After the end of the stress transition period (time t2), controller 130 sets a period of a normal in-vehicle environment (neutral period), in which controller 130 sets partition 121, the pair of side sections 122, and rear section 123 to the transparent state (non-blocking state). At this time, inducer 120 need not be operated.

Further, when inducer 120 is operated in the neutral period, controller 130 may set special lighting such as a blue sky by lighting 124, or generate road noise or talking voice by music player 125.

When the duration of a stress transition period is too long, the mental state of inducing subject 2 becomes excessively stressed. Then, by the transition from a stress transition period to a neutral period, the mental state of inducing subject 2 is held in the stressed state.

Note that the length of the stress transition period (time t1 to t2) may be appropriately changed based on the arrival time of inducing subject 2 at the destination. For example, the stress transition period may be a time until when it is determined that inducing subject 2 has transitioned to the stressed state according to a change in the state information acquired by information acquirer 110, or may be a preset time. The determination as to whether the mental state has transitioned to the stressed state may be made based on the degree of change in the state information or the subjectivity of inducing subject 2.

After the end of the neutral period (time t3), controller 130 provides a relaxation period in which inducing subject 2 is made relaxed. The stressed state is a mental state corresponding to the second quadrant in the mental coordinate system, and is a mental state in which the positive and negative relationships in the vertical and horizontal axes are inverted compared to the fourth quadrant corresponding to the relaxed state.

Note that the neutral period may be appropriately set to a time during which at least the stressed state of inducing subject 2 is maintained, based on the arrival time of inducing subject 2 at the destination. Further, under the circumstances in which the period needs to transition from the stress transition period to the relaxation period, such as a case where a period to get in vehicle 1 is short, the neutral period may be zero.

By the transition from the stressed state to the relaxed state, that is, a mental state in which the positive and negative relationships in the vertical and horizontal axes are inverted, the degree of change in the amount of transition of the mental state increases for inducing subject 2, and thus inducing subject 2 can easily realize that he/she is in a relaxed state.

The relaxation period may include a period during which inducing subject 2 is transitioned from a state other than the relaxed state to the relaxed state in the mental coordinate system, and a period during which the relaxed state in the mental coordinate system is maintained.

Specifically, controller 130 sets partition 121, the pair of side sections 122, and rear section 123 to a non-transparent state (blocking state). Then, controller 130 displays, for example, an image of natural scenery on partition 121, the pair of side sections 122, and rear section 123.

In addition to the image, controller 130 may also output special lighting such as a blue sky or sunlight filtering through trees in the forest by lighting 124, may generate a combination of a natural sound and BGM by music player 125, or may generate an aroma causing emotional healing such as a healing aroma by scent generator 126. The combination of a natural sound and BGM is, for example, a healing sound that heals the heart of a person, such as twittering of birds or murmur of a small stream. Further, controller 130 may combine and output two or more of the image, lighting, music, and aroma.

Note that the operation contents of inducer 120 in a relaxation period include an action increasing the degree of comfort and decreasing the degree of wakefulness in the mental coordinate system. The operation contents are not limited to the above examples and may be appropriately set according to an experiment or the like.

As described above, by providing the relaxation period depending on the riding time (stress transition period and neutral period) and the mental state (stressed state) of inducing subject 2, inducing subject 2 can be easily induced to the relaxed state (see FIG. 2).

Further, inducing subject 2 possibly desires to be awake after being relaxed. For example, in a situation where, after a conference (first conference) or the like is held, inducing subject 2 gets into vehicle 1 and moves to the next location of a second conference to participate in the second conference, inducing subject 2 possibly desires to relieve the stress held in the first conference and participate in the second conference in a refreshed state (awaking state).

In this case, controller 130 provides an awaking period in which inducing subject 2 is transitioned from a relaxed state to an awaking state, by operating inducer 120 as a blocking state in the relaxation period. The awaking period is a period including a falling-asleep transition period and an awaking transition period.

The falling-asleep transition period is a period for further lowering the degree of wakefulness in the relaxed state in the mental coordinate system, and is a period for causing inducing subject 2 to fall asleep. The awaking transition period is a period for inducing inducing subject 2 to an awaking state through the falling-asleep transition period.

Since inducing subject 2 is awake in the awaking state, transitioning inducing subject 2 to the awaking state with the degree of sleepiness being increased can cause inducing subject 2 to easily feel the effect of being refreshed, and therefore, the falling-asleep transition period is provided.

For example, controller 130 provides the falling-asleep transition period after the end of the relaxation period (time t4).

Note that the relaxation period is a time period that can be appropriately changed based on the arrival time of inducing subject 2 at the destination. For example, the relaxation period may be a time until when it is determined that inducing subject 2 has transitioned to the relaxed state according to a change in the state information acquired by information acquirer 110, or may be a preset time. The determination as to whether the mental state has transitioned to the relaxed state may be made based on the degree of change in the state information or the subjectivity of inducing subject 2.

Specifically, controller 130 sets partition 121, the pair of side sections 122, and rear section 123 to a non-transparent state (blocking state). Controller 130 then displays, for example, a completely dark image on partition 121, the pair of side sections 122, and rear section 123.

Further, in addition to the image, controller 130 may adjust and output lighting so that the lighting gradually becomes darker by lighting 124, or may generate a combination of a natural sound and BGM by music player 125. The combination of a natural sound and BGM is, for example, a sleep induction sound that induces sleepiness of a human, such as a wave sound. In addition, controller 130 may combine and output two or more of the image, lighting, and sound.

Note that the operation contents of inducer 120 in a falling-asleep transition period are information including an action maintaining the degree of comfort within the fourth quadrant and further decreasing the degree of wakefulness in the mental coordinate system. The operation contents are not limited to the above examples and may be appropriately set according to an experiment or the like.

Figure 5A:
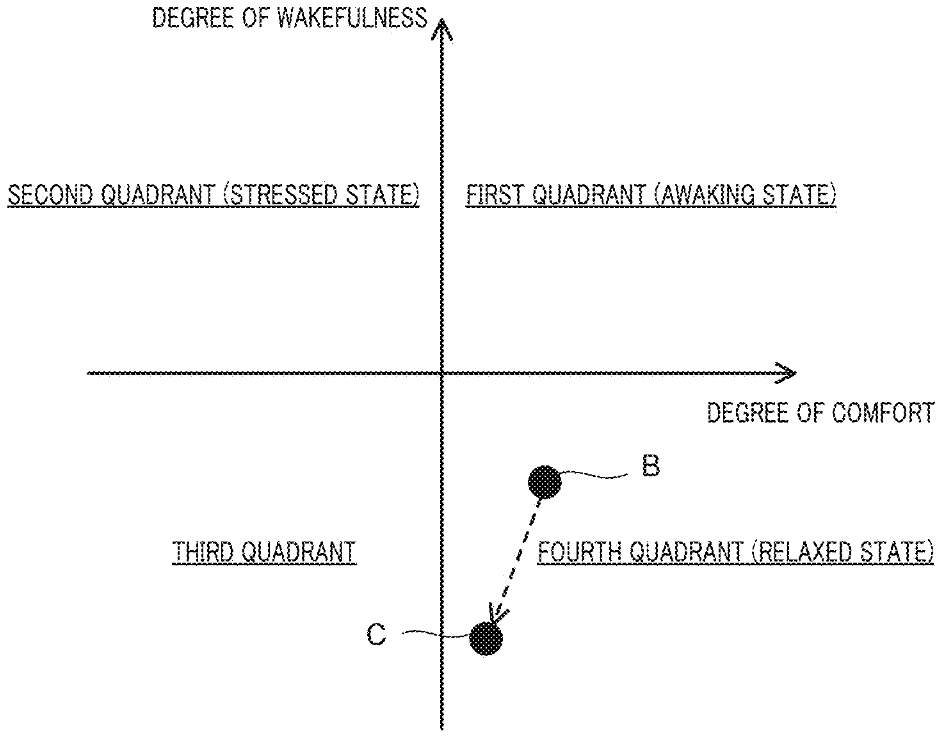
FIG. 5A illustrates another exemplary transition of the mental state in the mental coordinate system.

In this way, for example, as illustrated in FIG. 5A, the mental state of inducing subject 2 can be transitioned from point B in the region corresponding to the fourth quadrant to point C at which the degree of wakefulness is lower in the mental coordinate system.

Controller 130 provides an awaking transition period after the end of the falling-asleep transition period (time t5 in FIG. 4).

Note that the length of the falling-asleep transition period may be appropriately set based on the arrival time of inducing subject 2 at the destination. For example, the falling-asleep transition period may be a time until when it is determined that inducing subject 2 has transitioned to the state of falling asleep according to a change in the state information acquired by information acquirer 110, or may be a preset time. The determination as to whether the mental state has transitioned to the state of falling asleep may be made based on the degree of change in the state information or the change in the body movement or pupil diameter of inducing subject 2.

Specifically, controller 130 sets partition 121, the pair of side sections 122, and rear section 123 to a non-transparent state (blocking state). Controller 130 then displays, for example, an image of causing inducing subject 2 to be conscious of waking up on partition 121, the pair of side sections 122, and rear section 123. The image of causing inducing subject 2 to be conscious of waking up is, for example, an image of the rising sun or an image of mountain flowers.

In addition to the image, controller 130 may adjust and output lighting so that the lighting gradually becomes brighter by lighting 124, generate a lively, cheerful, or active music by music player 125, or generate a scent that makes the waking-up refreshing, such as a citrus aroma, by scent generator 126. Further, controller 130 may combine and output two or more of the image, lighting, music, and aroma.

Note that the operation contents of inducer 120 in an awaking transition period are information including an action maintaining the degree of comfort within the first quadrant and the fourth quadrant and increasing the degree of wakefulness in the mental coordinate system. The operation contents are not limited to the above examples and may be appropriately set according to an experiment or the like.

Transitioning the mental state of inducing subject 2 so that the degree of sleepiness of inducing subject 2 in the relaxed state increases as described above can increase the amount of transition of the mental state at the time of the transition to the awaking state.

Figure 5B:
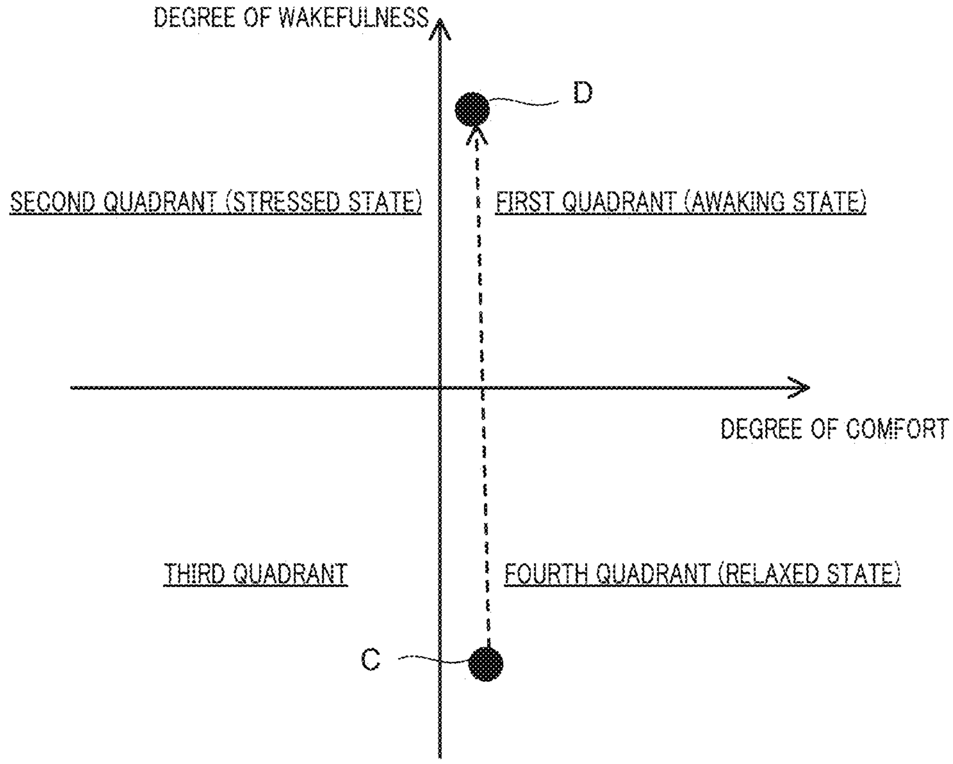
FIG. 5B illustrates still another exemplary transition of the mental state in the mental coordinate system.

For example, as illustrated in FIG. 5B, the mental state of inducing subject 2 is transitioned from point C where the degree of wakefulness is considerably low in the fourth quadrant (relaxed state) in the mental coordinate system to point D whether the degree of wakefulness is considerably high in the first quadrant (awaking state).

This makes it easy for inducing subject 2 to feel refreshed, thereby allowing inducing subject 2 to attend the second meeting in a perfect mental condition.

Further, controller 130 ends the awaking period depending on the arrival time of inducing subject 2 at the destination (time t6 in FIG. 4). When ending the awaking transition period, controller 130 sets partition 121, the pair of side sections 122, and rear section 123 of inducer 120 to the transparent state (non-blocking state), for example.

The timing of ending the awaking period may be any timing as long as the timing is before the arrival time at the destination. For example, the timing of ending the awaking period may be any timing as long as the timing is after the time when inducing subject 2 is determined to be transitioned to the awaking state according to the change in the state information acquired by information acquirer 110.

Further, controller 130 may adjust the awaking period depending on the arrival time of inducing subject 2 at the destination. For example, when it is desired to increase the ratio of the relaxation period, the timing of starting the awaking period may be delayed, or when the arrival time at the destination is delayed, the timing of ending the awaking period may be delayed.

Controller 130 may also allow inducing subject 2 to operate inducer 120 after the awaking period ends.

For example, after the awaking period ends, inducing subject 2 possibly desires to maintain the state of the awaking period, such as inducing subject 2 desires to keep the active music playing. Further, after the awaking period ends, inducing subject 2 desires to be in the relaxation period to see the image of the natural scenery displayed during the relaxation period.

In this case, controller 130 allows inducing subject 2 to select the state of inducer 120, so that inducing subject 2 can set the in-vehicle environment to the desired period. The target to be operated by inducing subject 2 may be, for example, a selection switch provided in vehicle 1 or a selection screen of a display device of vehicle 1.

Further, there may be a case where the initial mental state of inducing subject 2 is identified as a relaxed state, or a case where the mental state need not be transitioned to an awaking state after being brought into a relaxed state in the relaxation period. In this case, controller 130 provides a relaxation period to maintain the relaxed state of inducing subject 2.

Specifically, controller 130 sets partition 121, the pair of side sections 122, and rear section 123 to the transparent state (non-blocking state) as in the neutral period described above. At this time, inducer 120 need not be operated.

Further, controller 130 may operate inducer 120 by setting partition 121, the pair of side sections 122, and rear section 123 to the non-transparent state (blocking state) depending on a change in the state information acquired by information acquirer 110. Specifically, when there is a change in the state information such that the mental state of inducing subject 2 moves outside of the fourth quadrant in the mental coordinate system, such as a case where the degree of comfort decreases or the degree of wakefulness increases, controller 130 may operate inducer 120 by setting partition 121, the pair of side sections 122, and rear section 123 to the non-transparent states (blocking state).

In this way, the mental state of inducing subject 2 who gets in the vehicle can be maintained in a relaxed state.

Figure 6:
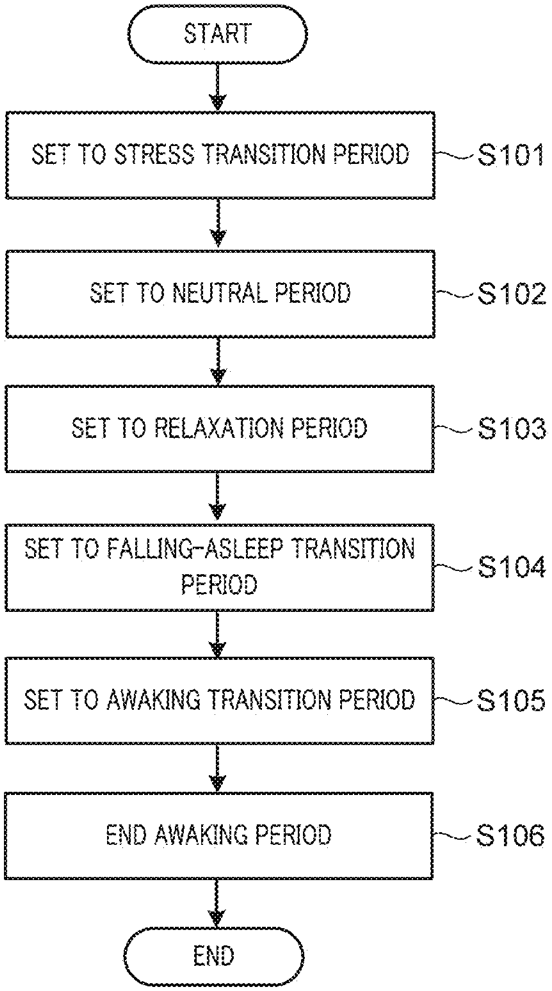
FIG. 6 is a flowchart illustrating an exemplary operation of inducing control in the inducing apparatus.

Next, an exemplary operation of inducing apparatus 100 is described. FIG. 6 is a flow chart illustrating an exemplary operation of inducing control in inducing apparatus 100. The processing in FIG. 6 is appropriately executed, for example, at a timing when inducing subject 2 gets in vehicle 1 and vehicle 1 starts.

As illustrated in FIG. 6, controller 130 provides a stress transition period (step S101). After the stress transition period ends, controller 130 provides a neutral period (step S102).

After the neutral period ends, controller 130 provides a relaxation period (step S103). After the relaxation period ends, controller 130 provides a falling-asleep transition period (step S104).

After the falling-asleep transition period ends, controller 130 provides an awaking transition period (step S105). Then, controller 130 ends the awaking period (Step S106), and the present control ends.

According to the present embodiment configured as described above, since inducer 120 is configured to be capable of blocking outside-vehicle information, it is possible to induce the mental state of inducing subject 2 to a predetermined state after blocking the outside-vehicle information.

Consequently, the mental state of the inducing subject can be correctly induced to a predetermined state without being interfered with the outside-vehicle information.

Further, the relaxation period is provided, so that inducing subject 2 who gets in the vehicle can be correctly induced to the relaxed state.

Furthermore, inducing subject 2 is induced to the awaking state through the relaxation period, which can make the amount of transition of the mental state in the mental coordinate system relatively large. This makes it easy for inducing subject 2 to feel the effect of being refreshed.

In addition, inducing subject 2 is induced to the relaxed state through the stress transition period, which can make the amount of transition of the mental state in the mental coordinate system relatively large. This makes it easy for inducing subject 2 to feel the effect of relaxation.

Further, the awaking period is adjusted depending on the arrival time of inducing subject 2 at the destination, so that the awaking period can be flexibly increased and deceased depending on the situation.

Furthermore, allowing inducing subject 2 to operate inducer 120 after the awaking period ends makes it possible to set the in-vehicle environment to the one suited to the mood of inducing subject 2.

Moreover, the pair of side sections 122 and rear section 123 have the same configurations as partition 121, which makes it possible to completely block outside-vehicle information from the periphery of inducing subject 2. Consequently, the mental state of inducing subject 2 can be induced further appropriately.

Note that, in the above-described embodiment, partition 121, the pair of side sections 122, and rear section 123 block the outside-vehicle information from inducing subject 2, but the present disclosure is not limited thereto, and the outside-vehicle information may be blocked by other than partition 121, the pair of side sections 122, and rear section 123. For example, an advancing/retreating member may be provided. The advancing/retreating member is configured to be capable of advancing and retreating with respect to the space inside the vehicle, advances to the field of view of the inducing subject when the outside-vehicle information is to be blocked, and retreats to the outside of the field of view of the inducing subject when outside-of vehicle information is not blocked.

In addition, the pair of side sections 122 and rear section 123 are provided in the above-described embodiment, but the present disclosure is not limited thereto, and the pair of side sections 122 and the rear section need not be provided as long as the forward field of view of the inducing subject can be blocked.

Further, the relaxation period is provided through the stress transition period in the above-described embodiment, but the present disclosure is not limited thereto, and the relaxation period may be provided without the stress transition period.

In addition, the awaking transition period is provided through the falling-asleep transition period in the above-described embodiment, but the present disclosure is not limited thereto, and the awaking period may be set without through the falling-asleep transition period.

Further, the awaking period is provided through the relaxation period in the above-described embodiment, but the present disclosure is not limited thereto, and the awaking period need not be provided through the relaxation period.

Further, in the above-described embodiment, the mental state of inducing subject 2 seated on back seat 1A is induced, but the present disclosure is not limited thereto, and the mental state of inducing subject 2 seated on front seat 1B may be induced only when autonomous driving or the like is in operation.

In addition, in the above-described embodiment, the initial mental state of inducing subject 2 is identified based on the change in the state information. However, the present disclosure is not limited thereto, and the initial mental state may be identified based on the subjective mental state of inducing subject 2.

The embodiments above are no more than specific examples in carrying out the present disclosure, and the technical scope of the present disclosure is not to be construed in a limitative sense due to the specific examples. That is, the present disclosure may be implemented in various forms without departing from the spirit thereof or the major features thereof.

The disclosure of Japanese Patent Application No. 2022-025945, filed on Feb. 22, 2022, including the specification, drawings and abstract, is incorporated herein by reference in its entirety.

INDUSTRIAL APPLICABILITY

The inducing apparatus of the present disclosure is useful as an inducing apparatus capable of correctly inducing a mental state of an inducing subject into a relaxed state.

The invention claimed is:

1. An inducing apparatus, comprising:

an inducer that induces an induced subject in a vehicle to a predetermined mental state, the inducer provided within a field of view of the induced subject, capable of blocking outside-vehicle information within the field of view, and capable of operating to induce the mental state; and a processor that controls the inducer:

to be in a blocking state in which the outside-vehicle information is blocked, to induce the induced subject to a relaxed state, and to be in a non-blocking state in which the outside-vehicle information is not blocked, to induce the mental state of the induced subject to remain in the relaxed state.

2. The inducing apparatus according to claim 1, wherein the processor induces the mental state of the induced subject to transition from the relaxed state to an awaking state by controlling the inducer to remain in the blocking state in which the outside-vehicle information is blocked.

3. The inducing apparatus according to claim 2, wherein the processor adjusts a period of time for inducing the mental state of the induced subject to the awaking state depending on an arrival time of the induced subject at a destination.

4. The inducing apparatus according to claim 2, wherein the processor allows the induced subject to operate the inducer after a period of time for inducing the mental state of the induced subject to the awaking state ends.

5. The inducing apparatus according to claim 1, wherein the inducer includes a partition that is placed at a boundary between a front seat and a rear seat of the vehicle and configured to be switchable between a transparent state and a non-transparent state, the transparent state making the outside-vehicle information in the non-blocking state, and the non-transparent state making the outside-vehicle information in the blocking state.

6. The inducing apparatus according to claim 5, wherein the inducer includes a first side section and a second side section which are respectively situated to the right and left of the induced subject, the first side section and the second side section configured to be switchable between the non-blocking state and the blocking state, and the processor synchronizes and controls the partition, the first side section, and the second side section.

7. The inducing apparatus according to claim 5, wherein the inducer includes a rear section that is provided behind the induced subject and configured to be switchable between the non-blocking state and the blocking state, and the processor synchronizes and controls the partition and the rear section.

8. The inducing apparatus according to claim 1, wherein the processor identifies the mental state of the induced subject based on one or more measurement results of heart rate information, pulse information, respiratory information, blood pressure information, electrocardiogram information, electroencephalogram information, body surface temperature information, pupil diameter information, electromyogram information, or body movement information of the induced subject.

9. The inducing apparatus according to claim 1, wherein the inducer includes at least one of lighting capable of adjusting brightness of a space in which the induced subject is located, a music player capable of playing music in the space in which the induced subject is located, or a scent generator capable of generating a scent in the space in which the induced subject is located, and the processor operates at least one of the lighting, the music player, or the scent generator.

10. The inducing apparatus according to claim 1, wherein the processor controls the inducer to induce the mental state of the induced subject to a stressed state and then to the relaxed state.

11. The inducing apparatus according to claim 1, wherein:

the processor controls the inducer to induce the mental state of the induced subject to transition from the relaxed state to a state of falling asleep, and to induce the mental state of the induced subject to transition from the state of falling asleep to an awaking state; and the processor causes the inducer to display image information to induce the mental state of the induced subject into the state of falling asleep.

12. An inducing apparatus, comprising:

an inducer that induces an induced subject in a vehicle to a predetermined mental state, the inducer provided within a field of view of the induced subject, capable of blocking outside-vehicle information within the field of view, and capable of operating to induce the mental state; and a processor that controls the inducer:

to display image information, to induce the mental state of the induced subject to a relaxed state, to be in a non-blocking state in which the outside-vehicle information is not blocked, to induce the mental state of the induced subject to remain in the relaxed state, and to display the image information, to induce the mental state of the induced subject to transition from the relaxed state to an awaking state.

* * * * *